(12) United States Patent
Souza et al.

(10) Patent No.: US 11,033,623 B1
(45) Date of Patent: *Jun. 15, 2021

(54) MAGNETIC STEM CELL THERAPY FOR LESIONS

(71) Applicant: GREINER BIO-ONE NORTH AMERICA, INC., Monroe, NC (US)

(72) Inventors: Glauco Souza, Houston, TX (US); Hubert Tseng, Houston, TX (US)

(73) Assignee: GREINER BIO-ONE NORTH AMERICA, INC., Monroe, NC (US)

( * ) Notice: Subject to any disclaimer, the term of this patent is extended or adjusted under 35 U.S.C. 154(b) by 78 days.

This patent is subject to a terminal disclaimer.

(21) Appl. No.: 16/002,960

(22) Filed: Jun. 7, 2018

Related U.S. Application Data

(63) Continuation of application No. 14/723,461, filed on May 28, 2015, now abandoned, which is a continuation-in-part of application No. 14/536,388, filed on Nov. 7, 2014, now Pat. No. 9,688,955, which is a continuation of application No. 13/393,651, filed as application No. PCT/US2010/050445 on Sep. 27, 2010, now Pat. No. 8,883,471.

(60) Provisional application No. 62/033,017, filed on Aug. 4, 2014, provisional application No. 62/005,383, filed on May 30, 2014, provisional application No. 61/245,846, filed on Sep. 25, 2009.

(51) Int. Cl.
| | |
|---|---|
| *A61K 41/00* | (2020.01) |
| *C12N 5/0775* | (2010.01) |
| *A61K 9/00* | (2006.01) |
| *A61K 45/06* | (2006.01) |
| *A61L 15/44* | (2006.01) |
| *A61L 15/36* | (2006.01) |
| *A61K 35/48* | (2015.01) |
| *A61K 35/34* | (2015.01) |
| *A61K 35/51* | (2015.01) |
| *A61K 35/28* | (2015.01) |
| *A61K 35/35* | (2015.01) |
| *A61K 35/545* | (2015.01) |
| *A61K 35/12* | (2015.01) |

(52) U.S. Cl.
CPC ........ *A61K 41/0052* (2013.01); *A61K 9/0019* (2013.01); *A61K 35/28* (2013.01); *A61K 35/34* (2013.01); *A61K 35/35* (2013.01); *A61K 35/48* (2013.01); *A61K 35/51* (2013.01); *A61K 35/545* (2013.01); *A61K 45/06* (2013.01); *A61L 15/36* (2013.01); *A61L 15/44* (2013.01); *C12N 5/0667* (2013.01); *A61K 2035/124* (2013.01); *A61L 2300/64* (2013.01); *C12N 2500/20* (2013.01); *C12N 2500/24* (2013.01)

(58) Field of Classification Search
None
See application file for complete search history.

(56) References Cited

PUBLICATIONS

Ito, Akira, et al. "A new methodology of mesenchymal stem cell expansion using magnetic nanoparticles." Biochemical Engineering Journal 20.2-3 (2004): 119-125. (Year: 2004).*

* cited by examiner

*Primary Examiner* — Robert J Yamasaki
(74) *Attorney, Agent, or Firm* — Boulware & Valoir (57) ABSTRACT

Magnetic cells plus a magnet are used to treat ED and other bodily lesions, whereby the magnetic cells are held in at or near the location of the lesion with a magnetic field for a period of time until efficacy is established. The cells can be any cell type, including stem cells, autologous cells, recombinant cells, combinations thereof and the like.

17 Claims, 8 Drawing Sheets

MAGNETIC STEM CELL THERAPY FOR LESIONS

PRIOR RELATED APPLICATIONS

This application is a continuation of U.S. Ser. No. 14/723,461, filed May 28, 2015, which claims priority to U.S. Ser. No. 62/033,017 filed Aug. 4, 2014, and also to 62/005,383 filed May 30, 2014; U.S. Ser. No. 14/723,461 is also a continuation-in-part of U.S. Ser. No. 14/536,388, filed Nov. 7, 2014, which is a continuation of U.S. Ser. No. 13/393,651, filed Mar. 1, 2012, which is a § 371 National Stage filing of PCT/US2010/050445, filed Sep. 27, 2010, which claims priority to U.S. Ser. No. 61/245,846, filed Sep. 25, 2009. Each of these applications is incorporated by reference herein in its entirety for all purposes.

FEDERALLY SPONSORED RESEARCH STATEMENT

Not applicable.

FIELD OF THE DISCLOSURE

The disclosure generally relates to stem cell therapies for erectile dysfunction, incontinence, cardiovascular disease, wounds, and other diseases, as well as materials, methods and systems for same.

BACKGROUND OF THE DISCLOSURE

Figure 1:
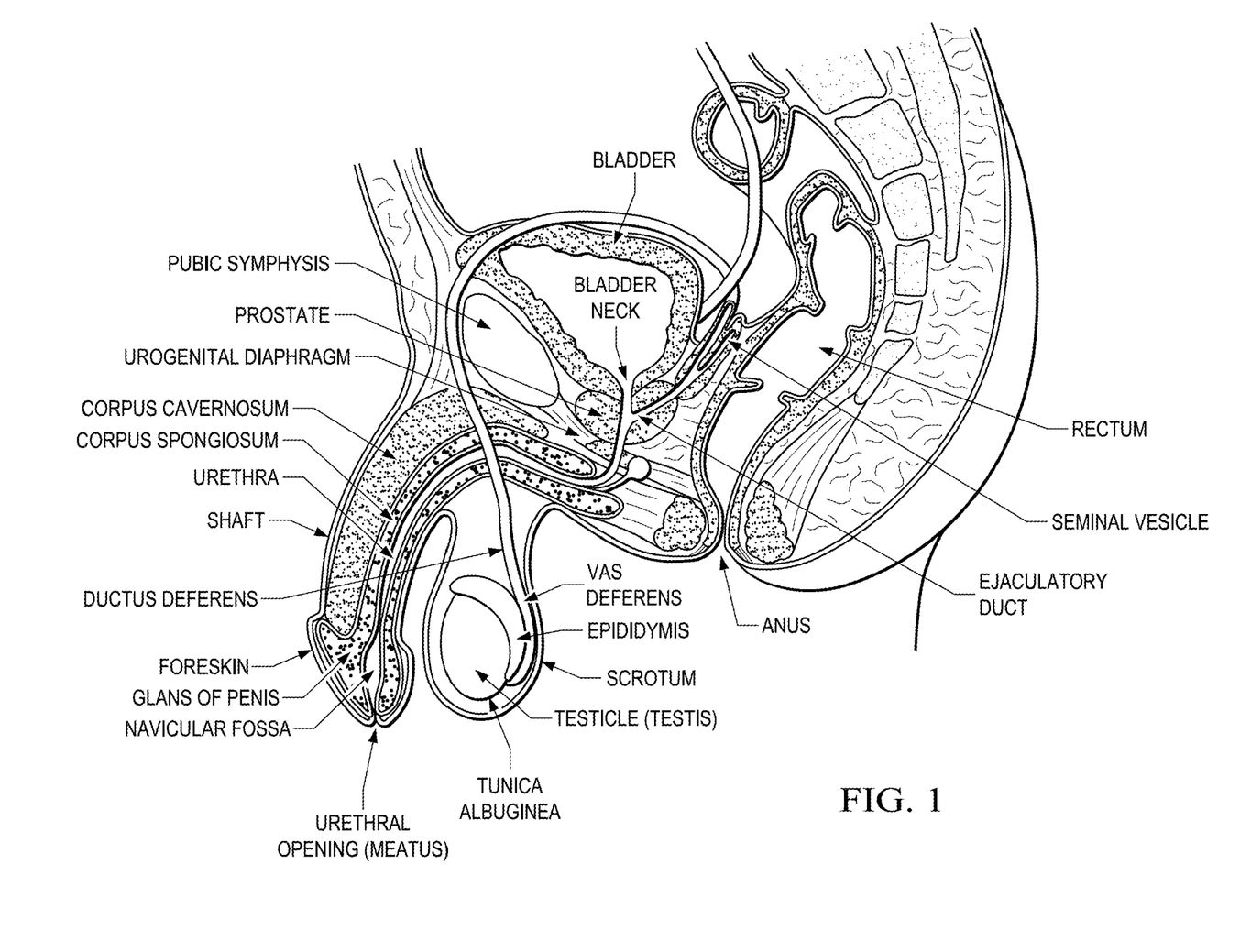
FIG. 1. Male urogenital anatomy.
Figure 2:
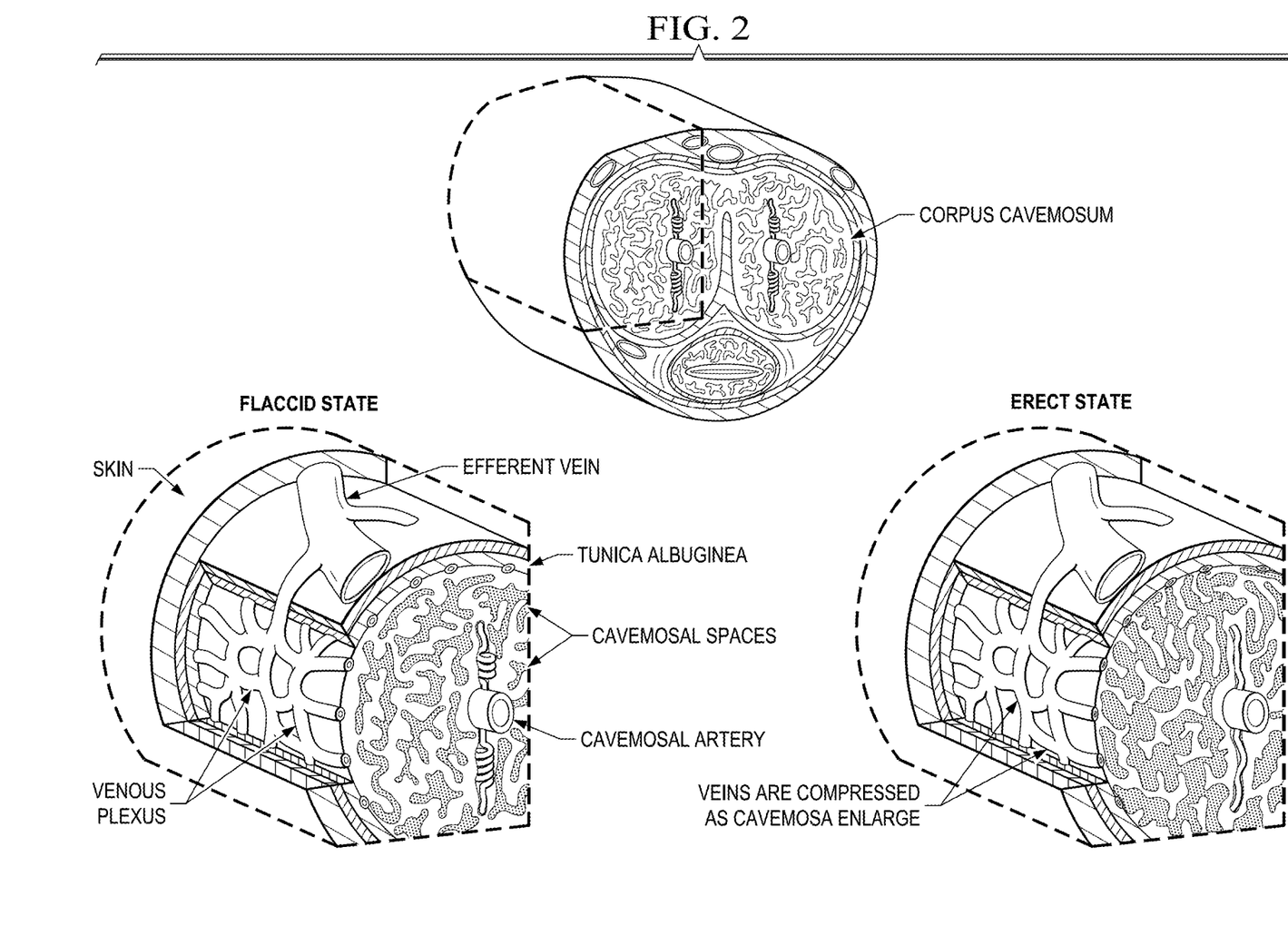
FIG. 2 Mechanics of erection. (A) In the flaccid state, arterial vessels are constricted and venous vessels are non-compressed. (B) On erection, smooth muscle relaxation in the trabeculae and arterial vasculature results in increased blood flow, which rapidly fills and dilates the cavernosal spaces. Venous outflow drops as the expanding cavernosal spaces compress the venous plexus and the larger veins passing through the tunica albuginea.

The anatomy of penis is illustrated in FIG. 1. Erection of the penis is the ultimate result of three complex biological activities. First, arterial dilation increases blood inflow to the penis. At the same time, the relaxation of smooth muscle of the corpus cavernosum allows an increase in size, thus increased blood storage in the penis. Additionally, penile venous occlusion decreases the blood outflow from the penis. The mechanics of erection is shown in FIG. 2.

The principal mediator of penile erection is nitric oxide (NO). NO is produced by both neuronal nitric oxide synthase (nNOS) in the nonadrenergic noncholinergic (NANC) nerves and endothelial nitric oxide synthase (eNOS) in the endothelium of penile arteries and cavernosal sinusoids. NO formed in nerves or endothelial cells then diffuses to neighboring smooth muscle cells and activates soluble guanylyl cyclase. This activation results in increased cGMP formation, which mediates smooth muscle relaxation.

Besides NO, other molecules such as vasoactive intestinal polypeptide (VIP), calcitonin gene-related peptide (CGRP), substance P, and pituitary adenylate cyclase-activating polypeptide (PACAP) are also important for penile erection.

Causes contributing to erectile dysfunction (ED) can be broadly classified into two categories: organic and psychological. Aging, vascular diseases, neurological injuries, diabetes mellitus are the common causes of organic ED. Depressive stress is the common cause of psychological ED. ED is also commonly caused by injuries that occur post prostatectomy and post radiotherapy, and a small number of cases are Peyronie's Disease-Associated ED.

Although the treatment of ED with oral phosphodiesterase type V (PDE5) inhibitors (sildenafil, tadalafil, and vardenafil) is effective in a wide range of individuals with ED, it is not efficacious in all patients. For example, the response rate to sildenafil decreased from 72% in men 18-49 years of age to 53% in men 50 years and older. The failure of sildenafil therapy occurs mainly in men with diabetes, non-nerve sparing radical prostatectomy, and those with high disease severity. Therefore, improved therapies based on a better understanding of the fundamental issues in erectile physiology and pathophysiology are still needed.

One approach for treating ED has been gene therapy. eNOS, CGRP, SOD and RhoA/Rho Kinase have all been used for gene therapy treatments, with some limited success. Although intracavernosal injection of adenovirus or adeno-associated virus containing eNOS, CGRP, SOD, or a dominant-negative RhoA mutant can augment erectile responses in aged or diabetic animals with ED, the disadvantage of this therapeutic strategy, such as local inflammatory responses and random transgene expression in almost all cell types, could limit its application to human patients.

Recently, intracavernous injection of stem cells has also shown some promise for erectile dysfunction. Stem cell (SC) therapy for ED has been investigated in 35 published studies, with one being a small-scale clinical trial. Out of these 35 studies, 19 were concerned with cavernous nerve (CN) injury-associated ED while 10 with diabetes mellitus-(DM-) associated ED. Adipose-derived SCs (ADSCs) were employed in 18 studies while bone marrow SCs (BMSCs) were used in 9 studies.

Transplantation of SCs was done mostly by intracavernous (IC) injection, as seen in 25 studies. Allogeneic and xenogeneic transplantations have increasingly been performed but their immune-incompatibility issues were rarely discussed. More recent studies also tend to use combinatory therapies by modifying or supplementing SCs with angiogenic or neurotrophic genes or proteins. All studies reported better erectile function with SC transplantation, and the majority also reported improved muscle, endothelium, and/or nerve in the erectile tissue.

However, differentiation or engraftment of transplanted SCs has rarely been observed; thus, paracrine action is generally believed to be responsible for SC's therapeutic effects. Further, most stem cells were washed out immediately, due to the communication between corpus cavernosum and the blood circulation. Keeping stem cells in the corpus cavernosum after intracavernous injection maybe a key step for successful stem cell therapy for ED.

What is needed in the art are better methods cell therapy that allow improved retention of cells, giving them sufficient time for cell growth and/or attachment or otherwise allowing their incorporation into the lesion being treated. Such a method would have application in ED and in other tissues where cell retention may be an issue due to cell wash out, such as in the arteries, veins, valves, heart, and the like.

SUMMARY OF THE DISCLOSURE

N3D Biosciences, Inc. has developed novel materials to allow magnetic nanoparticles to enter or adhere to cells, and with the use of a strong magnetic field can be levitated, printed to complex 3D cultures of cells for use in various methods, such as lung tissue replacement, and the like. See US20120171744 et seq. In addition, the company has developed a full suite of tools for the growth and manipulation of levitating cells and/or cultures.

Herein we have used these materials and tools for a novel method of treatment involving adding a magnetized cells to lesion in a body cavity or tissue, holding the magnetized cell in place with a magnetic field gradient for a time sufficient to allow incorporation, attachment and/or growth of said cells. The cells can be any cell, but in some instances will be stem cells. The stem cells are preferably autologous, e.g. derived from the patient, e.g., patient derived adipose tissue stem cells. If desired, the cells could also be recombinant, including a gene encoding one or more desired products.

Another embodiment is a novel method of treating male ED and/or incontinence, wherein stem cells are magnetized, e.g., according to the methods and materials described in US20120171744, injected into the penis, e.g., into the intercavernous spaces, and then held in place with the use of a magnet, which can be exterior or interior, although exterior magnets will likely be preferred.

A magnet can be held in place with the simple used of adhesive tape, but it would be preferred to use special underwear or other garment or device with a pocket into which the magnets can be placed. Alternatively, magnets can be attached to an adhesive bandage, specially designed and shaped for this use.

Figure 3A:
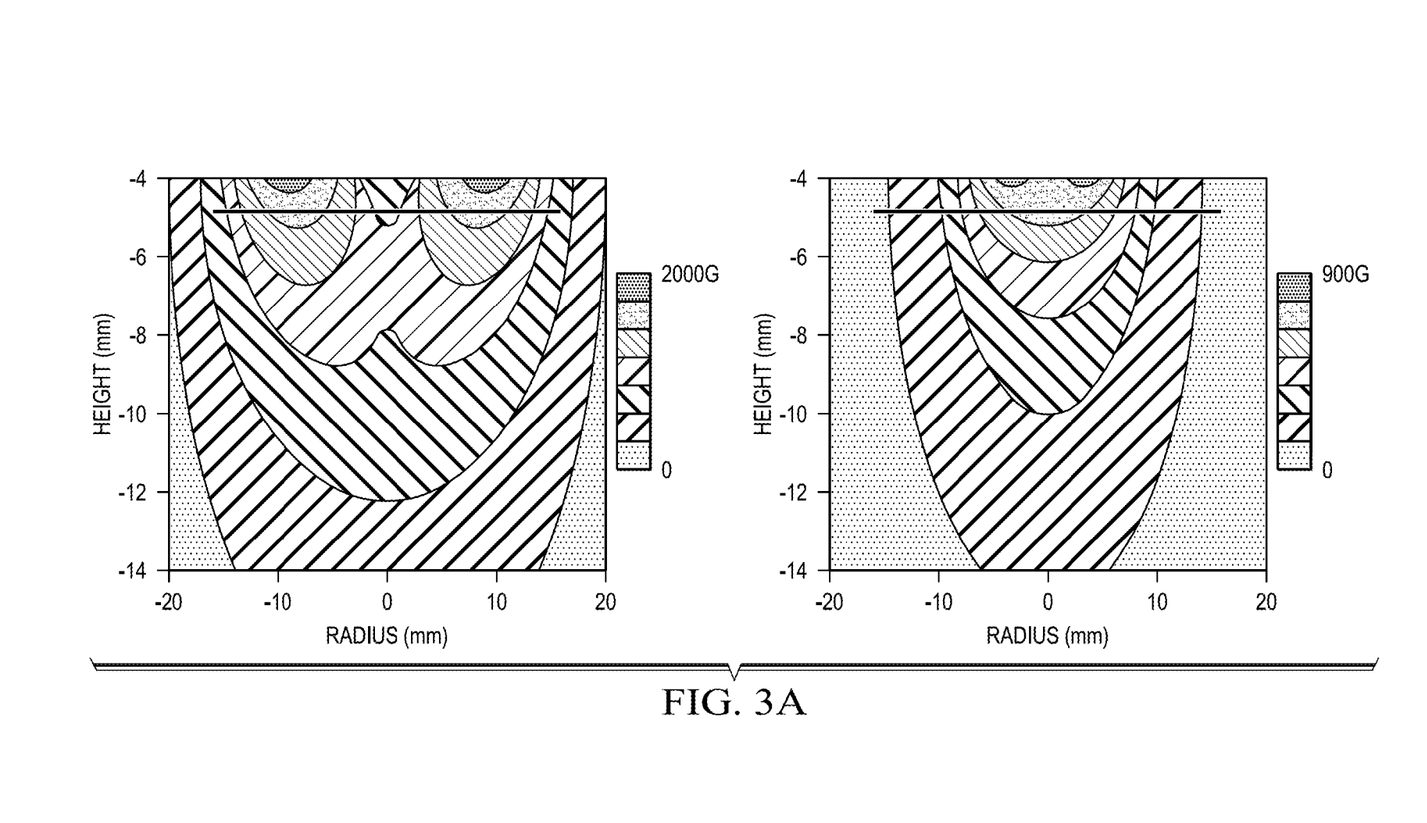
FIG. 3A. Estimated magnetic field profiles obtained by direct integration of the Biot-Savart law using Mathematica. On the left is a 2000 G ring magnet, and on the right a 9000 G disc magnet.
Figure 3B:
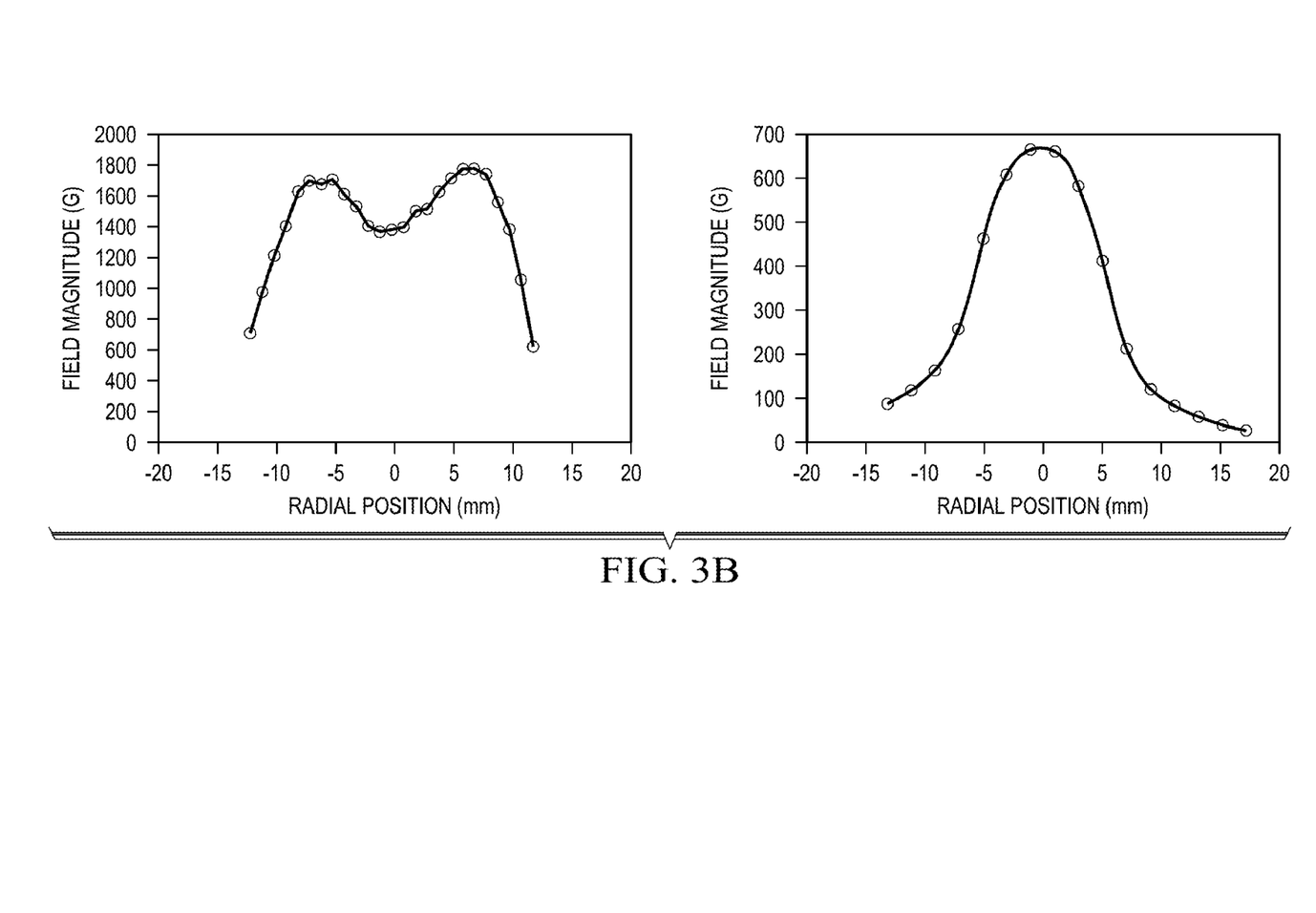
FIG. 3B. Hall probe measurements along a diameter perpendicular to the symmetry axis at the air-medium interface.

The magnet should be of high strength, preferably about 50-300 G, but the magnetic field gradient strength needed to manipulated the magnetic stem cells will vary, depending on the level of magnetic nanoparticles that are associated with the cells, and the distance the magnet is from the cells. A graph of estimated and measured field strength versus height is shown in FIG. 3. The lowest possible field strength is preferred, as exposure to low magnetic fields (30-500 G) has no major effect on cell proliferation, metabolism or inflammatory response, although magnetic fields of higher strength (800-4,000 G) may influence cell behavior.

The magnetic field for the weakest magnet used to date for cell levitation in a petri plate was approximately 200 G at the bottom of the petri dish, and the gradient was approximately 50 G/mm. These conditions yield a magnetization of about 20 emu/g and a force of 7 pN, which is just enough to levitate the cells off the bottom of the dish.

Although we specifically have implemented and tested ED treatment in animal models, we expect that that the inventive method can be applied to other organs or body cavities. Thus, arteriole or venous injections with magnetic cells, e.g., magnetic stem cells, can be performed, the cells held in place for a period of time using the requisite magnetic field, and thus successful treatment of lesions effected. This might be particularly beneficial in patients with poor peripheral blood flow for a variety of reasons. Likewise, the heart, bronchial tubes, pulmonary spaces, lymphatic tissue and other body cavities or tubes can be injected, and cells held in the required location for a period of time need to establish cell adherence and eventual efficacy. Similarly, surface wound can be treated using e.g. wound dressing containing magnetized cells and a magnet. Do Generally, the materials for magnetizing stem cells have three components—a positively charged nanoparticle, a negatively charged nanoparticle, and a support molecule, loosely tying the three components together in an intimate admixture. One of the two nanoparticles must be magnetically responsive, but obviously either one could contain this feature.

Preferred materials include positively and negatively charged nanoparticles, one of which must contain or be one or more magnetically responsive elements, such as iron oxide. These nanoparticles are further combined with a polymer, preferably a natural or cell-derived polymer, or other long molecule that acts as a support (herein called a "support molecule") for the charged nanoparticles and the cells, holding the nanoparticles in place for their uptake or adsorption by the cells. The inclusion of both positive and negative nanoparticles allows intimate admixing of the nanoparticles and drives the assembly of the three components, thus ensuring even distribution and good uptake. The support molecule intimately combines all three components with the cells in fibrous mat-like or tangled structure that allows the stem cells to take up the magnetically responsive element.

The magnetically responsive element can be any element or molecule that will respond to a magnetic field, e.g., rare earth magnets (e.g., samarium cobalt (SmCo) and neodymium iron boron (NdFeB)), ceramic magnet materials (e.g., strontium ferrite), or the magnetic elements (e.g., iron, cobalt, and nickel and their alloys and oxides). Particularly preferred are paramagnetic materials that react to a magnetic field, but are not magnets themselves, as this allows for easier assembly of the materials. A preferred material is magnetic iron oxide (MIO) nanoparticles ($Fe_3O_4$, magnetite) of about 10-100 nm size range.

The cells need to take up enough magnetic nanoparticle so as to be levitated in the magnetic field, but not so much as to disrupt the cells normal metabolism. Levels of about 30-150 pg/cell, or about 50 pg of MIO are typical.

The negatively charged nanoparticles include charge stabilized metals (e.g. silver, copper, platinum, palladium), but preferably is a gold nanoparticle since gold is largely inert in the body.

The positively charged nanoparticles include surfactant or polymer stabilized or coated alloys and/or oxides (e.g. elementary iron, iron-cobalt, nickel oxide), and preferably is an iron oxide nanoparticle.

The nanoparticles should have a nano-scale size, and thus are about 100 nm. Size can range, however, between about 5-250 nm, 50-200 nm, 75-150 nm, but they can be smaller or larger, provided only that the size is appropriate to allow entry or adsorption to the cell type in use. We have shown previously that there is an upper limit on the effective size of the magnetic nanoparticle, and micrometer size is too big for effectiveness, although some functionality was still observed.

As used herein a "positively charged nanoparticle" or "positive nanoparticle" is defined as any particle less than 200 nm, preferably 100 nm or less, that has an overall or net positive charge. Preferably, the particle is non-toxic, but this is not essential as the particles do not remain with the cells long term.

As used herein a "negatively charged nanoparticle" or "negative nanoparticle" is defined as any particle less than 200 nm, preferably 100 nm or less, and most preferably about 2-25 nm, that has an overall negative charge. Preferably, the particle is non-toxic, but this is not essential as the particles do not remain with the cells for a long period of time.

As used herein "support molecule" refers to any long molecule that will interact with the nanoparticles to create a mat-like or felt-like fibrous structure or gel and thus hold the magnetic nanoparticle in close proximity with the cell for uptake.

Any of the three components can be functionalized, derivatized, or coated so as to further promote interaction of the components and/or the stem cells, or to encourage stem cell attachment and growth in the penis, body cavity or other tissue. Thus, one or more members can be functionalized, derivatized, or coated with an antibody that e.g., binds to a cell surface antigen. Other binding pairs included receptors-ligands, biotin-strepavidin, complementary nucleic acids, wheat germ agglutinin (WGA), sialic acid containing molecules, and the like.

Coatings can also include protective or passivating coatings, particularly for the nanoparticles, such as PVP, dextran, BSA, PEG, and the like. The nanoparticles, especially the nanoparticle that comprises the magnetically responsive element, can be labeled for visualization, e.g., with a fluorophore, radiolabel, or the like, particularly during the development and in vitro testing of magnetized stem cells. However, for actual therapeutic uses, it may be preferred to omit such labels.

The word "lesion" herein is used in its broadest sense, meaning any abnormality or damage in any tissue or part of an living organism, usually caused by disease, genetic defect, age, injury or trauma.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, growth factors and the like.

The following abbreviations are used herein:

| ABBREVIATION | TERM |
| --- | --- |
| ADSC | Adipose-derived SC |
| BCNC | bilateral cavernous nerve crush |
| CC | corpus cavernosum |
| CN | cavernous nerve |
| DM | diabetes mellitus |
| ECG | electrocardiogram |
| ED | Erectile Dysfunction |
| EPC | endothelial progenitor cell |
| ESC | embryonic stem cells |
| IC | intracavernous |
| LAD | left anterior descending coronary artery |
| LV | left ventricle |
| MI | Myocardial infarction |
| MSC | mesenchymal stem cells |
| SC | Stem cell |

BRIEF DESCRIPTION OF THE DRAWINGS

FIG. 5A-G. Magnetic dressing.

DETAILED DESCRIPTION

The disclosure provides novel method of cell therapies for any lesion, wherein magnetic cells are created using e.g., the methods of US20120171744. These cells are injected into the lesion and held in place with the use of an external magnet. The results showed improved cell retention, giving the cells the time needed for growth, attachment and differentiation.

The novel methods can be applied to any tissue or part or a patient, but are expected to be particularly beneficial in body cavities, where cells would otherwise have a tendency to wash away with the movement of body fluids. Thus, the methods have particular use in the urogenital tracts, the gastroenteric tract, the cardiovascular system, the pulmonary system, the lymphatic system, and the like.

Lesions that can be treated in the way include heart and vascular damage of all types, especially arising from heart attack, arteriosclerosis, stent damage, trauma, and the like. Other lesions include damage to the urethra, e.g., through treatment of prostate cancer, damage to the vas deferens, e.g., from vasectomy, treatment of ED, treatment of other symptoms caused by damage to bodily lesions.

The disclosure also provides novel method of stem cell therapy of ED. Magnetic stem cells are created using e.g., the methods of US20120171744. These cells are injected into the intracavernous spaces and held in place with the use of an external magnet. The results showed improved cell retention, giving the stem cells the time needed for growth, attachment and differentiation.

In more detail, the invention comprises one or more of the following embodiments, in any combination:

A method of treating a lesion in a patient, comprising injecting or otherwise adding magnetic cells into or near a lesion in a patient, and holding said magnetic cells in place using a magnet for a period of time sufficient for the growth and/or attachment of said magnetic cells.

A method of treating a lesion in a patient, comprising injecting magnetic stem cells at or near a lesion in a patient, and holding said magnetic stem cells in place using a magnet for a period of time sufficient for the growth and/or attachment of said magnetic stem cells.

A method of treating a bodily lesion comprising injecting magnetic cells in the bodily space of a patient with a lesion in or affecting said bodily space, and holding said magnetic cells in place using a magnet for a period of time sufficient for the growth and/or attachment of said magnetic cells.

A method of treating a bodily lesion comprising injecting magnetic stem cells in the bodily space of a patient with a lesion in or affecting said bodily space, and holding said magnetic stem cells in place using a magnet for a period of time sufficient for the growth and/or attachment of said magnetic stem cells.

A method of treating erectile dysfunction (ED) and/or incontinence comprising injecting magnetic stem cells in penis of a patient with ED, and holding said magnetic stem cells in place using a magnet for a period of time sufficient for the growth and attachment of said magnetic stem cells.

A method of treating erectile dysfunction (ED) comprising injecting magnetic stem cells in the intracavernous space of a patient with ED, and holding said magnetic stem cells in place using a magnet for a period of time sufficient for the growth and attachment of said magnetic stem cells.

A method wherein said magnetic stem cells are adipose-derived stem cells.

A method wherein said magnetic stem cells are allogenic.

A method further comprising isolating adipose-derived stem cells from said patient, and adding a magnetizing reagent comprising magnetic nanoparticles to said adipose-derived stem cells, and incubating said magnetizing reagent and adipose-derived stem cells for a time sufficient to allow said adipose stem cells to uptake said magnetic nanoparticles.

A method wherein said stem cells are selected from a group consisting of adipose stem cell, bone marrow stem cells, testis stem cells, bone marrow mononuclear cells, endothelial progenitor cells, umbilical cord blood stem cells, umbilical cord blood and tissue stem cells, and skeletal muscle-derived stem cell.

A composition comprising magnetic stem cells plus a protein or gene encoding same selected from VEGF, eNOS, nNOS, NANC, VIP, CGRP, SOD, RhoA and PACAP.

A composition wherein said stem cells are selected from a groups consisting of adipose stem cell, bone marrow stem cells, testis stem cells, bone marrow mononuclear cells, endothelial progenitor cells, umbilical cord blood stem cells, umbilical cord blood and tissue stem cells, and skeletal muscle-derived stem cell.

A composition comprising stem cells with at least 50 pg of iron oxide associated therewith.

A composition wherein said magnetic stem cells are allogenic or allogenic adipose-derived stem cells.

A composition wherein said stem cells are selected from a group consisting of adipose stem cell, bone marrow stem cells, testis stem cells, bone marrow mononuclear cells, endothelial progenitor cells, umbilical cord blood stem cells, umbilical cord blood and tissue stem cells, and skeletal muscle-derived stem cell.

Erectile Dysfunction

To demonstrate proof of concept in ED treatment, we used an animal model and adipose-derived stem cells.

Adipose-derived stem cells (ADSCs) were isolated from inguinal fat tissue of adult male Sprague-Dawley rats. ADSCs at third generation were cultured at a 70-80% confluence in 10 cm cell culture dish, and then incubated with NanoShuttle (8 mL/cm$^2$ of the cell culture surface area) overnight to allow for cell binding.

The DMEM/F12 medium with NanoShuttle was replaced by the fresh DMEM/F12 after cell binding, and the Nano-ADSCs were ready to use for our study. For tracking purposes, all cells to be used for transplantation were labeled for 30 minutes with 5-Chloromethylfluorescein Diacetate (CellTracker™ Green CMFDA, Life Technologies Corporation, Grand Island, N.Y., USA) before ICI. Approximately 1×10$^6$ CellTracker™-labeled cells in 0.2 ml of PBS were used for each IC injection.

ED animal models were created by bilateral cavernous nerve crush (BCNC) injury of rats and randomly assigned into three groups.

Group A: ADSCs IC injection.
Group B: ADSCs with nanoparticle IC injection.
Group C: ADSCs with nanoparticle IC injection+magnet probes. The magnets were positioned outside the penis near the corpus cavernosum so as to keep a minimal distance between magnet and cells.

Rats were sacrificed at day 1, 3, 5 and 9 after IC injection, respectively. The rat penis was then harvested for tracking ADSCs by immunofluorescence. CellTracker™ Green CMFDA (5-Chloromethylfluorescein Diacetate) was used to track ADSCs present in the corpus cavernosum (CC).

Our in vitro studies showed that ADSCs with nanoparticles entrained therein promoted cell aggregation with the use of a magnet probe.

Our rat in vivo study with the immunofluorescence confirmed that ADSCs with nanoparticle were successfully maintained in the corpus cavernosum with the use of magnet probes for up to 9 days. Most ADSCs were washed out in other groups in day 1 and 3 after IC injection. From this, we can see that the tethering of magnetic cells in a patient with the use of a magnetic field gradient significantly improves cell retention and incorporation in the lesion.

Intracavernous injection of stem cells therapy for ED has shown some effectiveness in experimental studies, but it is believed that the stems cells provide a systemic treatment rather than local therapy since most of the cells wash out of the corpus cavernosum. Studies show that cells usually need 4-6 hours to accustom to a new circumstance and attach to the surface of the plate. However, blood flow washes stem cells away from the CC immediately after injection, and this makes it almost impossible for stem cells to settle down in the CC.

We have successfully demonstrated the use of magnetic force to hold the stem cells in the CC after IC injection. The magnetic force produced by magnets kept the magnetized ADSCs in the CC for 6 hours—which should be enough for active stem cells to attach to the surface of the CC. Once the stem cells adhere, they can grow freely with the supply from blood circulation. Our study proved that the majority of injected stem cells could be successfully kept in the CC up to three days, by CellTracker™ visualization. We further proved that the cells could stay in the CC up to 28 days by immunohistochemistry. Also, we demonstrated this new approach could effectively improve erectile function as well as improve endothelial and smooth muscle function compared with controls. This is a key step to making stem cell therapy an actual local therapy for ED.

Magnetic nanoparticle is a novel technology to improve ADSCs therapy for ED in an animal model, and we predict that the technique can be applied to human males as well. However, there are some issues to address before using the technique in humans.

First, the dosage of ADSCs was the traditional dosage used for stem cell injection, which is likely to be too high using our new approach, as indicated by some neoplasms observed in the CC. Thus, in the next phase, we will optimize the best dosage using the magnetic retention approach. Also the characteristics of the neoplasm will be studied.

Second, we observed that some Nanoshuttle™ remained in the CC. Although a previous study and our in vitro study showed NanoShuttle™ bound stem cells grew regularly up to 25 days, any long term effects of NanoShuttle™ in cells needs to be explored. Also, we will optimize the level of NanoShuttle™ for cell binding in the next phase.

Third, we have not determined how the retained stem cells grow and coordinate with original residents and how it improves the erectile function. Further research is ongoing to determine these underling mechanisms.

Myocardial Infarction

Figure 4A:
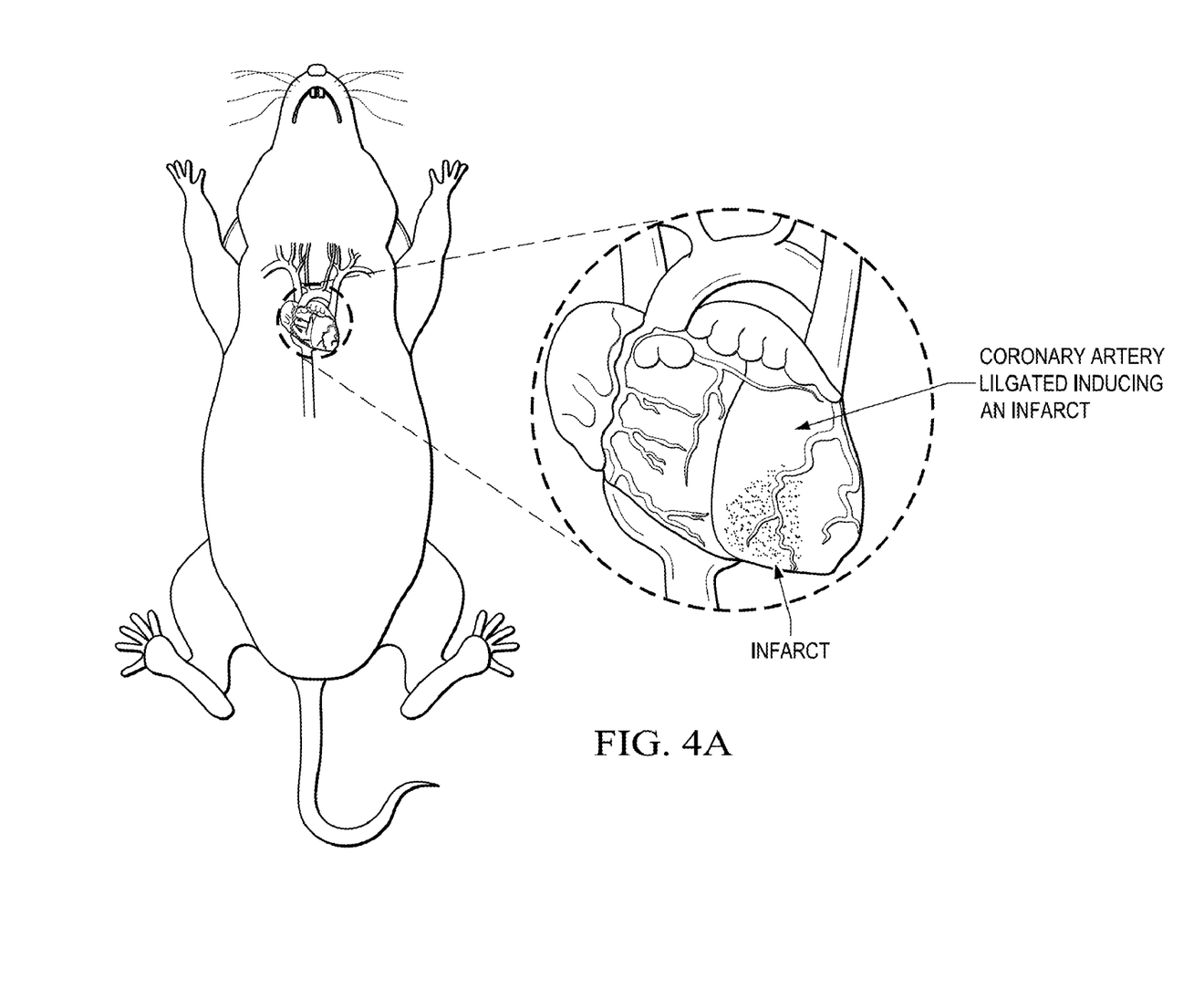
FIG. 4A Animal model for myocardial infarction.
Figure 4B:
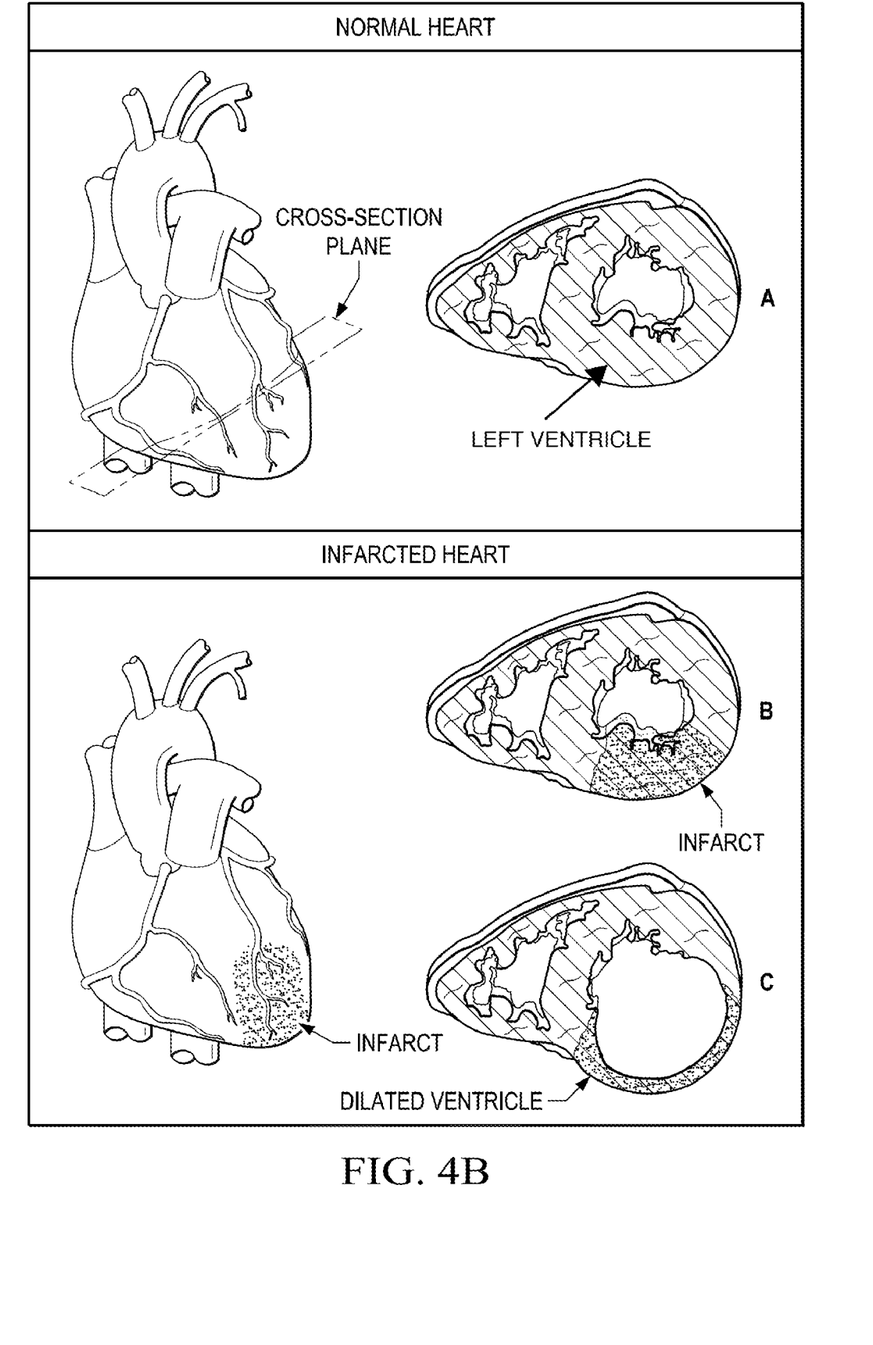
FIG. 4B. Illustration of normal (A) vs. Infarcted Heart (B). The left ventricle has a thick muscular wall, shown in cross-section in (A). After a myocardial infarction (heart attack), heart muscle cells in the left ventricle are deprived of oxygen and die (B), eventually causing the ventricular wall to become thinner (C).

An animal model of myocardial infarction (MI) can be used to demonstrate proof of concept of the method in cardiovascular lesions. Typical myocardial infarction is illustrated in FIG. 4A, and the comparison between normal and infarcted hearts is shown in FIG. 4B.

Ligation of the left anterior descending coronary artery (LAD) in a rodent (e.g., rabbit or mice) to create anterior wall infarction of the left ventricle (LV) has been described by many workers. The surgical procedure is divided into three steps. In brief, the heart of an animal under anesthesia is exposed following a left thoracotomy at the fourth intercostal space. The pericardium is carefully broken and the LAD ligated with a suture placed just distally (1 mm) from tip of the left auricle. The procedure is considered successful if the electrocardiogram (ECG) shows ST-segment elevation and the anterior wall of the left ventricle becomes whitish. Finally, the lungs are inflated and the chest closed.

This permanent ligation of the LAD can cause irreversible damage to the myocardium, which is stable and easily reproduced. It has been extensively employed in studies on MI therapy using techniques such as; cell implantation, genetic modification and the administration of cytokines. Further ligation of the LAD can also produce a HF model or an ischemia-reperfusion model by subsequently removing the occlusion.

Studies using myocardial infarct animal models have indicated that transplantation of mesenchymal stem cells (MSC), umbilical cord blood cells, bone-marrow-derived haematopoietic stem cells, skeletal myoblasts, endothelial progenitor cell (EPC), cardiac stem cells, embryonic stem cells (ESC), or induced-pluripotent stem cells have the potential to improve the function of ventricular muscle after MI. Clinical trials have also produced some encouraging results.

Initial studies will be performed with umbilical cord blood cells or bone marrow derived MSC, which are readily available in this animal. The cells will be magnetized as above, injected into the left ventricle and held in place with a magnet, as described above. Success can be evaluated by Myocardial gated SPECT (multi-pinhole gated SPECT-CT system) to measure LV function and cardiac perfusion before, 1 week after MI, and 4 weeks and 8 weeks after stem cell therapy. PCR or Western blots can be used to measure levels of MI markers throughout the experiments, and histology can be used to evaluate the repair once the animal is sacrificed at 8 weeks. No stem cell sham control, and stem cells injected without an applied magnetic field will be the controls.

Lung Disease

An animal model of lung disease can be used to demonstrate proof of concept of the method in pulmonary lesions. An animal model of emphysema can be generated by elastase treatment. All-trans retinoic acid (ATRA) is known to reverse the anatomic and physiologic signs of pulmonary emphysema. Mice with elastase-induced emphysema can be treated with magnetic stem cells as described herein. Such treatments can be combined with all-trans retinoic acid (ATRA), granulocyte colony-stimulating factor (G-CSF), or a combination of both. ATRA or G-CSF promote lung regeneration and increased bone marrow-derived cell (BMC) numbers in alveoli. Combined treatment of both had an additive effect, which indicated that BMC mobilization might be important in lung regeneration.

Lung emphysema is induced in mice by intranasal instillation of porcine pancreas elastase (200 units/kg; SIGMA-ALDRICH®, St Louis, Mo., USA). Three weeks after elastase administration, mice are expected to exhibit emphysematous changes in the lungs. At this point, mice are randomly divided into four groups (each group n=5) and administered either vehicle only, vehicle plus magnetic stem cells, vehicle plus magnetic stem cells plus magnetic field. Mice are jacketed with a jacket that includes a breast pocket for an arc magnet or sham of equivalent weight (e.g., Rare Earth Neodymium Magnet Arc Segments Grade N42, Outside Diameter 1"×Inside Diameter 0.75"×Length 0.75" 90 Degree Angle—BrMax: 13200 gauss—available from magnet4less.com). Mice are maintained in the magnetic jacket for one week.

Emphysema is evaluated by morphometric analyses, including exercise capacity, shown by distance run and mean velocity, as well as elimination of carbon dioxide. Biomarkers are evaluated throughout the experiments by e.g., PCR and/or Western blot. The mice are sacrificed at the end of the experiments for histological analysis.

For the morphometric analysis, a motor-driven treadmill chamber for one animal (e.g., LE 8700, PANLAB®, Barcelona, Spain) is used. The speed of the treadmill and the intensity in milliamps of the electric shock applied to an stainless steel grid at the rear end of the treadmill are controlled by a potentiometer. Room air is pumped into the chamber at a controlled flow rate (700 ml/min) by a chamber air supplier (OXYLET LE 400, PANLAB®). Outflow is directed to an oxygen and carbon dioxide analyzer (Oxylet 00; PANLAB®) to measure consumption of oxygen and production of carbon dioxide. The mean room temperature is maintained at 21±1° C.

After an adaptation period of 40 min in the treadmill chamber the mice are exercised at different velocities, starting at 7.2 m/min and increasing the velocity 7.2 m/min every 10 min. The inclination of the treadmill is maintained at an uphill angle of 10°. Velocities are increased until the animal can no longer sustain a given speed and remained for more than ten seconds on the electrified grid, which provides an electrical stimulus (1 milliamp) to keep the mice running. Total running distance and running time are recorded. Treadmill tests are carried out on all mice before the induction of emphysema and 2, 4, 6 and 8 weeks after induction of emphysema.

Incontinence

Urinary incontinence and bladder dysfunction affect a large number of people, who experience a decreased quality of life due to social and sexual isolation as well as feelings of shame, anxiety, and depression. As the elderly population increases, both the number of people who have a decreased quality of life due to these conditions and the economic burden of treating these dysfunctions are expected to increase dramatically.

Stress urinary incontinence (SUI) is typically treated with pelvic floor exercises, a bulking agent, or surgery. Duloxetine, a pharmaceutical agent, is approved for SUI treatment in some countries, but is not approved for this indication in the United States. Surgery remains the gold standard for bothersome cases and options include a Burch colposuspension procedure, an autologous fascial sling, and a midurethral synthetic sling. The latter has become the most common operation for SUI due to its minimally invasive nature, ease of use, and good long-term efficacy with up to 11 years of follow-up. Nonetheless, up to a third of women undergo a second anti-SUI surgery due to recurrent SUI during their lifetime. In some patients, slings show no efficacy immediately after surgery and success rates decline steadily after surgery.

There is a lack of noninvasive therapy successful at treating SUI over the long term, suggesting the potential for development of innovative procedures such as stem cell therapy. Various techniques using cells derived from various tissues (e.g., adipose and muscle tissues) utilizing different application techniques have been tested in several different animal models of incontinence, one being a bilateral sciatic nerve transection model and another being a pudendal nerve denervation models, typically in rats.

In addition, there has already been some clinical work in this area. Early clinical trials testing stem cells as a treatment for incontinence have used autologous muscle-derived stem cells (MDSCs) that have been injected directly either transurethrally or periurethrally. A recent randomized blinded trial showed almost 50% improvement in patients 1 year after injection, although the study size was small (Herschorn 2010). ADSCs harvested and purified from lipoaspiration have also been injected periurethrally in two male patients after radical prostatectomy (Yamamoto 2010). Urinary incontinence progressively improved after 2 weeks of injection and persisted up to 12 weeks after treatment, with decreases in leakage volume and increases in quality of life, maximal urethral closure pressure, and functional urethral length. A bulking effect was demonstrated on magnetic resonance imaging 12 weeks after treatment, indicating that ADSCs may have contributed to the improvement of sphincteric function. Unfortunately, this work was later retracted due to a breach of ethical research guidelines, and therefore, needs to be repeated and validated under appropriate ethical research approval.

Nonetheless, these studies indicate that the use of magnetized stem cells held in the urethra with magnetic force may be a suitable treatment for incontinence and related disorders. Further, such tests are possible using allogenic stems cells obtained from adipose tissue, are minimally invasive, and thus such experiments are in the near future.

Magnetic Dressing

FIG. 5 shows a magnetic dressing. This is a simple way of keeping cells and/or magnetized material in place, at the same time protecting a wound with wound dressing material, and minimizing tissue damage from having to tear dressing material from deposited cells.

Figure 5A:
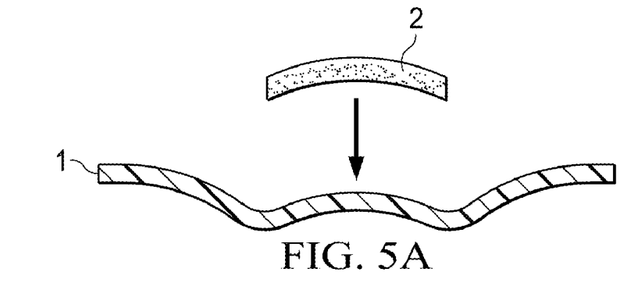
Figure 5B:
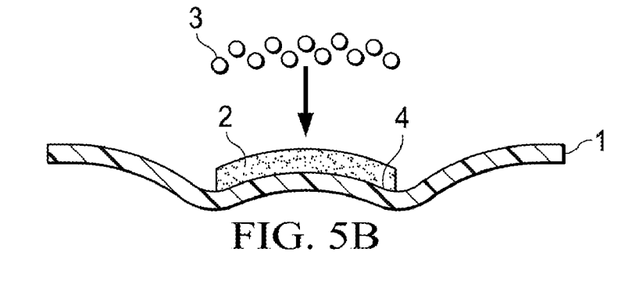
Figure 5C:
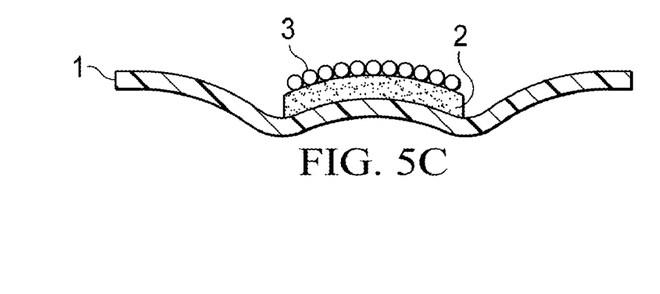
Figure 5D:
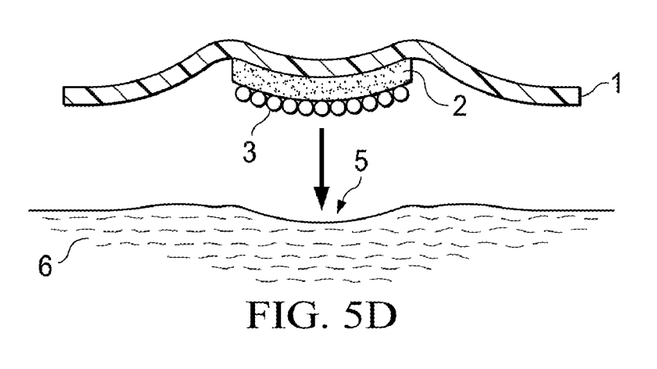
Figure 5E:
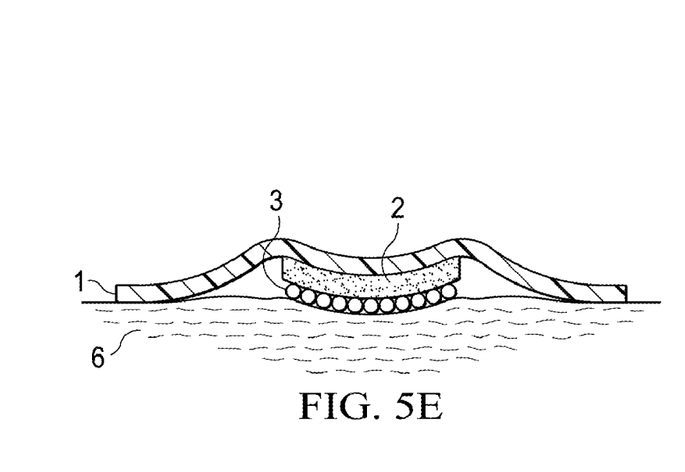
Figure 5F:
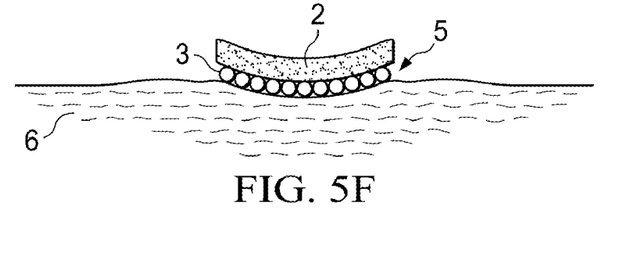
Figure 5G:
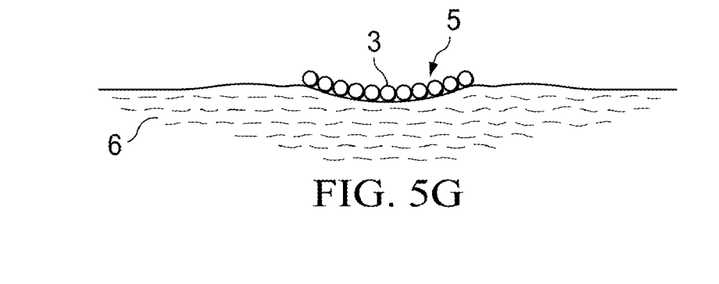

In more detail, FIG. 5A-C illustrates the process of generating or assembling a magnet dressing. Magnetic patch 1 is a single flexible magnet or an array of magnets, as appropriate for the area being treated. In FIG. 5B Sterile non-sticky dressing/gauze or "teflon" gauze 2 is placed adjacent magnet 1.

In FIG. 5C magnetized cells/material 3 is added to the magnetic dressing. This magnetized material 3 can be magnetized cells, or preferably magnetized 3D cultures or sheets or magnetized extra-cellular matrix e.g., from decellularized cultures, magnetic nanoparticles 4 carrying drugs therapeutic compounds.

In FIG. 5D the fully assembled magnetic dressing is applied to a wound 5, and possibly overlapping undamaged tissue 6. This could be left on for a short time e.g., 1-2 days or a long time, e.g. a week, depending on severity and responsiveness. Preferably, the dressing is left in place until cells adhere and begin to proliferate. In FIG. 5F, remove magnet 1 carefully, leaving the cells 3 under the gauze or other absorbent matrix 2. The cells 3 will transfer from the gauze 2 to the wound 5, which can be aided by the use of a magnet underneath the wound 5 to attract cells off the gauze 2 and onto the wound 5. If use under the wound is not possible, the magnet can be reversed such that the field is opposite. Eventually, the gauze can be removed as well, or in some instances the absorbent material may resorb into the tissue.

The following references are incorporated by reference in their entirety for all purposes herein.

US20120171744

WO2013019212

Deng W., et al., Gene and stem cell therapy for erectile dysfunction, *International Journal of Impotence Research* (2005) 17, S57-S63 (available online at http://www.nature.com/ijir/journal/v17/n1s/full/3901430a.html).

Ching-Shwun Lin, Advances in Stem Cell Therapy for Erectile Dysfunction, Advances in Andrology Volume 2014 (2014), Article ID 140618 (available online at http://www.hindawi.com/journals/aandrol/2014/140618/).

Herschorn S, et al. Autologous muscle-derived cells as therapy for stress urinary incontinence: a randomized, blinded trial. Neurourol Urodyn. 2010; 29(2):307.

Yamamoto T., et al. Periurethral injection of autologous adipose-derived stem cells for the treatment of stress urinary incontinence in patients undergoing radical prostatectomy: report of two initial cases (Retracted article. See vol. 17, pg. 896, 2010) Int J Urol. 2010; 17(1):75-82.

What is claimed is:

1. A method, comprising:
    a) obtaining stem cells;
    b) magnetizing said stem cells by incubation with a magnetic composition until said stem cells uptake said magnetic composition and become magnetic stem cells;
        i) said magnetic composition comprising an intimate fibrous mat admixture of i) a positively charged nanoparticle, ii) a negatively charged nanoparticle, and ii) a support molecule, wherein one of i) or ii) is a magnetically responsive material.

2. The method of claim 1, further comprising:
    a) adding said magnetic stem cells to a lesion in a patient, wherein said magnetic stem cells have about 30-150 pg/cell of magnetically responsive material; and
    b) holding said magnetic stem cells in place at said lesion using a magnet providing a magnetic field of 30-500 G for a period of time sufficient for the growth and attachment of said magnetic stem cells to said lesion.

3. The method of claim 2, wherein said lesion is erectile dysfunction (ED), and wherein magnetic stem cells are injected into a penis of a patient with ED, and said magnetic stem cells are held in place using a magnet placed adjacent said penis for a period of time sufficient for the growth and attachment of said magnetic stem cells.

4. The method of claim 2, wherein said lesion is a surface wound, and wherein magnetic stem cells are formed into a dressing with an absorbent matrix and a magnet and applied to said surface wound so that said cells are adjacent said wound.

5. The method of claim 2, wherein said lesion is a lesion in a vein, artery or heart, and wherein magnetic stem cells are injected into said vein, artery or heart, and said magnetic stem cells are held in place using a magnet placed adjacent said vein, artery or heart for a period of time sufficient for the growth and attachment of said magnetic stem cells.

6. The method of claim 2, wherein said lesion is a lesion in a urethra causing incontinence, and wherein magnetic stem cells are injected into a urethra of a male patient, and said magnetic stem cells are held in place using a magnet placed adjacent said penis for a period of time sufficient for the growth and attachment of said magnetic stem cells.

7. The method of claim 2, wherein said magnetic stem cells are allogeneic.

8. The method of claim 2, wherein said magnetic stem cells are autologous.

9. The method of claim 2, wherein said stem cells are selected from a group consisting of adipose stem cell, bone marrow stem cells, testis stem cells, bone marrow mononuclear cells, endothelial progenitor cells, umbilical cord blood stem cells, umbilical cord blood and tissue stem cells, and skeletal muscle-derived stem cells.

10. The method of claim 2, wherein said magnetic stem cells are adipose-derived stem cells.

11. The method of claim 10, further comprising isolating said adipose-derived stem cells from said patient.

12. The method of claim 11, wherein said magnetic composition comprises gold nanoparticles and magnetic iron oxide nanoparticles and said support molecule is polylysine.

13. The method of claim 2, wherein said stem cells are selected from a group consisting of adipose stem cell, bone marrow stem cells, testis stem cells, bone marrow mononuclear cells, endothelial progenitor cells, umbilical cord blood stem cells, umbilical cord blood and tissue stem cells, and skeletal muscle-derived stem cells.

14. The method of claim 2, wherein said magnetic stem cells are adipose-derived stem cells.

15. The method of claim 14, further comprising isolating said adipose-derived stem cells from said patient.

16. The method of claim 2, wherein said magnetic composition comprises gold nanoparticles and magnetic iron oxide nanoparticles and said support molecule is polylysine.

17. The method of claim 1, wherein said magnetic composition comprises gold nanoparticles and magnetic iron oxide nanoparticles and said support molecule is polylysine.

* * * * *